US005736124A

United States Patent [19]
Akehurst et al.

[11] Patent Number: 5,736,124
[45] Date of Patent: Apr. 7, 1998

[54] AEROSOL FORMULATIONS CONTAINING P134A AND PARTICULATE MEDICAMENT

[75] Inventors: Rachel Ann Akehurst; Anthony James Taylor; David Andrew Wyatt, all of Ware, Great Britain

[73] Assignee: Glaxo Group Limited, London, England

[21] Appl. No.: 453,820

[22] Filed: May 30, 1995

Related U.S. Application Data

[63] Continuation of Ser. No. 328,957, Oct. 24, 1994, abandoned, which is a continuation of Ser. No. 94,174, Aug. 5, 1993, abandoned.

[30] Foreign Application Priority Data

Dec. 12, 1991 [GB] United Kingdom ............. 9126444
Feb. 6, 1992 [GB] United Kingdom ............. 9202522

[51] Int. Cl.⁶ ............................................. A61K 9/12
[52] U.S. Cl. ............................................. 424/45; 424/46
[58] Field of Search ............................. 424/45, 46

[56] References Cited

U.S. PATENT DOCUMENTS

| | | | |
|---|---|---|---|
| 2,868,691 | 1/1959 | Porush et al. | 167/54 |
| 2,885,427 | 5/1959 | Rob et al. | 260/653.7 |
| 3,014,844 | 12/1961 | Thiel et al. | 167/82 |
| 3,219,533 | 11/1965 | Mullins | 167/82 |
| 3,320,125 | 5/1967 | Grim | 167/54 |
| 3,809,294 | 5/1974 | Torgeson | 222/182 |
| 3,897,779 | 8/1975 | Hansen | 128/266 |
| 4,044,126 | 8/1977 | Cook et al. | 424/45 |
| 4,174,295 | 11/1979 | Bargigia et al. | 252/305 |
| 4,347,236 | 8/1982 | Tanskanen | 424/45 |
| 4,405,598 | 9/1983 | Brown | 424/45 |
| 4,814,161 | 3/1989 | Jinks et al. | 424/45 |
| 5,118,494 | 6/1992 | Schultz et al. | 424/45 |
| 5,126,123 | 6/1992 | Johnson | 424/45 |
| 5,182,097 | 1/1993 | Byron et al. | 424/45 |
| 5,190,029 | 3/1993 | Byron et al. | 424/45 |
| 5,202,110 | 4/1993 | Dalby et al. | 424/45 |
| 5,225,183 | 7/1993 | Purewal et al. | 424/45 |
| 5,230,884 | 7/1993 | Evans | 424/45 |
| 5,348,730 | 9/1994 | Greenleaf et al. | 424/45 |
| 5,474,759 | 12/1995 | Fassberg et al. | 424/45 |
| 5,658,549 | 8/1997 | Akehurst et al. | 424/45 |
| 5,674,471 | 10/1997 | Akehurst et al. | 424/45 |
| 5,674,473 | 10/1997 | Purewal et al. | 424/45 |
| 5,681,545 | 10/1997 | Purewal et al. | 424/45 |
| 5,683,677 | 11/1997 | Purewal et al. | 424/45 |
| 5,695,743 | 12/1997 | Purewal et al. | 424/45 |

FOREIGN PATENT DOCUMENTS

| | | |
|---|---|---|
| 134923 | 2/1977 | Denmark. |
| 0 372 777 | 6/1990 | European Pat. Off.. |
| A-0 372 777 | 6/1990 | European Pat. Off.. |
| 0 504 112 | 9/1992 | European Pat. Off.. |
| A-0 504 112 | 9/1992 | European Pat. Off.. |
| 27 03 119 | 10/1990 | Germany. |
| 437766 | 3/1985 | Sweden. |
| 86/04233 | 7/1986 | WIPO. |
| A-86 04233 | 7/1986 | WIPO. |
| 90/07333 | 7/1990 | WIPO. |
| 91/04011 | 4/1991 | WIPO. |
| 91/11173 | 8/1991 | WIPO. |
| 91/11495 | 8/1991 | WIPO. |
| 91/11496 | 8/1991 | WIPO. |
| 91/14422 | 10/1991 | WIPO. |
| 92/00107 | 1/1992 | WIPO. |
| 92/06675 | 4/1992 | WIPO. |
| 92/08446 | 5/1992 | WIPO. |
| 92/08447 | 5/1992 | WIPO. |
| A-92 08446 | 5/1992 | WIPO. |
| 92/11190 | 7/1992 | WIPO. |
| 92/22287 | 12/1992 | WIPO. |
| 92/22288 | 12/1992 | WIPO. |
| 93/11743 | 6/1993 | WIPO. |
| 93/11744 | 6/1993 | WIPO. |
| 93/11745 | 6/1993 | WIPO. |
| 93/11747 | 6/1993 | WIPO. |

OTHER PUBLICATIONS

Oberholz, *Frankfurter Allgemeine Zeitung*, Oct. 1989, vol. 25, No. 207, p. 7.
Dalby et al., *Pharmaceutical Technology*, Mar. 1990, vol. 14, No. 3, pp. 26–33.
Amzacort™ carton, William H. Rorer, Inc., Fort Washington, Pennsylvania, USA 19034, 1986.
*Pharmaceutical Journal*, Sep. 29, 1990, vol. 245, pp. 428–429,.
*The Theory and Practice of Industrial Pharmacy*, 2nd Ed., 1976 (Philadelphia, PA: Lea and Febiger), pp. 270 and 276–278.
*Handbook of Aerosol Technology*, 2nd Edition, 1979 (New York, New York: Van Nostrand Reinhold Company), pp. 30, 32, 33, 166, 167, 232, 233.
U.S. Senate Hearings, 12–14 May 1987, 343–347, 437 (U.S. Government Printing Office, Washington, D.C., 1987), CIS:1987–S321–26.
*Hagers Handbook of Pharmaceutical Practice*, 1971, pp. 342–354 (Berlin: Spring–Verlag).

*Primary Examiner*—Raj Bawa
*Attorney, Agent, or Firm*—Bacon & Thomas

[57] ABSTRACT

This invention relates to aerosol formulations of use for the administration of medicaments by inhalation, in particular a pharmaceutical aerosol formulation which comprises particulate medicament, a fluorocarbon or hydrogen-containing chlorofluorocarbon propellant and up to 5% w/w based upon propellant of a polar cosolvent, which formulation is substantially free of surfactant. A method of treating respiratory disorders which comprises administration by inhalation of an effective amount of a pharmaceutical aerosol formulation as defined is also described.

43 Claims, No Drawings

AEROSOL FORMULATIONS CONTAINING P134A AND PARTICULATE MEDICAMENT

CROSS-REFERENCE TO RELATED APPLICATIONS

This application is a continuation of application Ser. No. 08/328,957, filed Oct. 24, 1994, now abandoned, which is a continuation of application Ser. No. 08/094,174, filed Aug. 5, 1993, which is a 371 application of PCT/EP92/02810 Dec. 4, 1992, published as WO93/11745 Jun. 24, 1993, now abandoned.

BACKGROUND OF THE INVENTION

1. Field of the Invention

This invention relates to aerosol formulations of use for the administration of medicaments by inhalation.

The use of aerosols to administer medicaments has been known for several decades. Such aerosols generally comprise the medicament, one or more chlorofluorocarbon propellants and either a surfactant or a solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

2. Description of the Prior Art

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP 0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

Thus, for example EP 0372777 requires the use or 1,1,1,2-tetrafluoroethane in combination with both a cosolvent having greater polarity than 1,1,1,2-tetrafluoroethane (e.g. an alcohol or a lower alkane) and a surfactant in order to achieve a stable formulation or a medicament powder. In particular it is noted in the specification at page 3, line 7 that "it has been found that the use of propellant 134a (1,1,1,2-tetrafluoroethane) and drug as a binary mixture or in combination with a conventional surfactant such as sorbitan trioleate does not provide formulations having suitable properties for use with pressurised inhalers". Surfactants are generally recognised by those skilled in the art to be essential components of aerosol formulations, required not only to reduce aggregation of the medicament but also to lubricate the valve employed, thereby ensuring consistent reproducibility of valve actuation and accuracy of dose dispensed. Whilst WO91/11173, WO91/11495 and WO91/14422 are concerned with formulations comprising an admixture of drug and surfactant, WO91/04011 discloses medicinal aerosol formulations in which the particulate medicaments are pre-coated with surfactant prior to dispersal in 1,1,1,2-tetrafluoroethane.

SUMMARY OF THE INVENTION

We have now surprisingly found that, in contradistinction to these teachings, it is in fact possible to obtain satisfactory dispersions of medicaments in fluorocarbon or hydrogen-containing chlorofluorocarbon propellants such as 1,1,1,2-tetrafluoroethane without recourse to the use of any surfactant in the composition, or the necessity to pre-treat the medicament prior to dispersal in the propellant.

There is thus provided in one aspect of the invention a pharmaceutical aerosol formulation which comprises particulate medicament, a fluorocarbon or hydrogen-containing chlorofluorocarbon propellant and up to 5% w/w based upon propellant of a polar cosolvent, which formulation is substantially free of surfactant. By "substantially free of surfactant" is meant formulations which contain no significant amounts of surfactant, for example less than 0.0001% by weight of the medicament.

The particle size of the particulate (e.g. micronised) medicament should be such as to permit inhalation of substantially all of the medicament into the lungs upon administration of the aerosol formulation and will thus be less than 100 microns, desirably less than 20 microns, and preferably in the range 1–10 microns, e.g. 1–5 microns.

Medicaments which may be administered in aerosol formulations according to the invention include any drug useful in inhalation therapy which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines and pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, orciprenaline, or (−)-4-amino-3,5-dichloro-α-[[[6-[2-(2-pyridinyl)ethoxy]hexyl]amino]methyl]benzene-methanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as add addition salts) or as esters (e.g. lower alkyl esters) or as solvates (e.g. hydrates) to optimise the activity and/or stability of the medicament and/or to minimise the solubility of the medicament in the propellant.

Particularly preferred medicaments for administration using aerosol formulations in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol, (e.g. as the xinafoate salt), terbutaline (e.g. as the sulphate salt), reproterol (e.g. as the hydrochloride salt), beciomethasone dipropionate, fluticasone propionate or (−)-4-amino-3,5-dichloro-α-[[[6-[2-(2-pyridinyl)-ethoxy]hexyl]amino]-methyl]benzenemethanol. Salmeterol, salbutamol, fluticasone propionate, beclomethasone dipropionate and physiologically acceptable salts and solyates thereof are especially preferred.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention further provides aerosol formulations in accordance with the invention which contain two or more particulate medicaments. Medicaments may be selected from suitable combinations of the medicaments mentioned hereinbefore. Thus, suitable combinations of bronchodilatory agents include ephedrine and theophylline, fenoterol and ipratropium, and isoetharine and phenylephrine aerosol formulations.

Preferred aerosol formulations in accordance with the invention comprise (a) an effective amount of a particulate bronchodilatory medicament (b) an effective amount of a particulate antiinflammatory, preferably a steroidal antiinflammatory medicament (c) a fluorocarbon or hydrogen—containing chlorofluorocarbon propellanr and (d) up to 5% w/w based upon propellant of a polar cosolvent. Particularly preferred aerosol formulations contain bronchodilators such as salbutamol (e.g. as the free base or as the sulphate salt), salmeterol (e.g. as the xinafoate salt) or isoprenaline in combination with an antiinflammatory steroid such as a beclomethasone ester (e.g. the diproprionate)or a fluticasone ester (e.g. the propionate). Alternatively aerosol formulations may contain a bronchodilator in combination with an antiallergic such as cromoglycate (e.g. the sodium salt). Combinations of isoprenaline and sodium cromoglyeate, salmeterol and fluticasone propionate; or salbutamol and beclomethasone dipropionate are especially preferred.

The final aerosol formulation desirably contains 0.005–10% w/w, preferably 0.005–5% w/w, especially 0.01–1.0% w/w, of medicament relative to the total weight of the formulation.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluoro carbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$hydrogen-containing fluorocarbons such as 1,1,1,2-tetrafluoroethane ($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

The propellant may additionally contain a volatile adjuvant such as a saturated hydrocarbon for example propane, n-butane, isobutane, pentone and isopentane or a dialkyl ether for example dimethyl ether. In general, up to 50% w/w of the propellant may comprise a volatile hydrocarbon, for example 1 to 30% w/w. However, formulations which are substantially free of volatile adjuvants are preferred.

Polar cosolvents which may be incorporated into the formulations according to the present invention include (e.g. $C_{2-6}$)aliphatic alcohols and polyols such as ethanol, isopropanol and propylene glycol and mixtures thereof. Preferably ethanol will be employed. In general only small quantities (e.g. 0.05 to 3.0% w/w) of polar cosolvent are required to improve the dispersion and the use of quantities in excess of 5% w/w may disadvantageously tend to dissolve the medicament. Formulations .preferably contain less than 1% w/w, e.g. about 0.1% w/w of polar cosolvent. Polarity may be determined for example, by the method described in European Patent Application Publication No. 0327777.

A particularly preferred embodiment of the invention provides a pharmaceutical aerosol formulation consisting essentially of one or more particulate medicament, one or more fluorocarbon or hydrogen-containing chlorofluorocarbon propellant and 0.01 to 5% w/w based upon propellant of a polar cosolvent.

The formulations of the invention may be prepared by dispersal of the medicament in the selected propellant in an appropriate container, e.g. with the aid of sonication. It may be preferred to add the cosolvent after the medicament and propellant have been combined in order to minimise any solubilising effects of the cosolvent and thereby enhance the dispersion. The process is desirably carried out under anhydrous conditions to obviate any adverse effects of moisture on suspension stability.

The formulations according to the invention form weakly flocculated suspensions on standing but, surprisingly, these suspensions have been found to be easily redispersed by mild agitation to provide suspensions with excellent delivery characteristics suitable for use in pressurised inhalers, even after prolonged storage. Minimising and preferably avoiding the use of formulation excipients e.g. surfactants in the aerosol formulations according to the invention is also advantageous since the formulations may be substantially taste and odour free, less irritant and less toxic than conventional formulations.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention is particularly impressive and may be measured by conventional techniques, for example by cascade impaction or by the "Twin Impinger" analytical process. As used herein reference to the "Twin Impinger"

assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention have been found to have a respirable fraction of 20% or more by weight of the medicament, preferably 25 to 70%, for example 30 to 60%.

Optionally, the medicament may be surface-modified prior to its dispersion in the propellant by treatment with a substantially non-polar liquid medium which is a non-solvent for the medicament. There is thus provided in a further aspect of the invention an aerosol formulation comprising particulate, surface-modified medicament, as defined herein, a fluorocarbon or hydrogen-containing chlorofluorocarbon propellant and up to 5% w/w based upon propellant of a polar cosolvent, which formulation is substantially free of surfactant. By "surface-modified medicament" is meant particles of medicament which have been surface-modified by admixture with a substantially non-polar non-solvent liquid, followed by removal of the liquid. The substantially non-polar non-solvent liquid medium is conveniently an aliphatic hydrocarbon, e.g. a lower alkane, which is sufficiently volatile to permit its ready evaporation, e.g. at ambient temperature and pressure, after slurrying with the medicament. The use of isopentane as liquid medium is particularly advantageous in this respect.

The medicament is desirably slurried with the liquid medium under anhydrous conditions to obviate any adverse effects of moisture on suspension stability. The slurry may advantageously be sonicated to maximise the surface-modifying effect of the treatment. The liquid may be removed by any convenient means for example by evaporation or by filtration followed by evaporation, provided that following treatment the medicament is substantially free of the liquid. The formulations of the invention will be substantially free of the non-solvent non-polar liquid.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF$_{30}$, DF60), Bespak plc, UK (e.g. BK300, BK356) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and a mixture of the polar cosolvent and liquified propellant is pressure filled through the charge vessel into a manufacturing vessel. The drug suspension is mixed before recirculation to a filling machine and an aliquot of the drug suspension is then filled through the metering valve into the canister. Alternatively, where the drug is particularly soluble in the polar cosolvent, the particulate medicament may be suspended in 50–90% w/w of the propellant before the cosolvent is added and then made up to weight with propellent before pressure filling into canisters. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Thus, for example, each valve actuation may deliver 25 microgram salmeterol, 100 microgram salbutamol, 25, 50, 125 or 250 microgram fluticasone propionate or 50, 100, 200 or 250 microgram beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Micronised salmeterol xinafoate (9.57 mg) was weighed directly into an open aluminium can. 1,1,1,2-Tetrafluoroethane (18.2 g) was added from a vacuum flask together with ethanol (182 mg) and a metering valve was crimped into place. The resulting aerosol contained 9.57 mg salmeterol xinafoate (1.0% w/w ethanol) and delivered 25 microgram salmeterol per actuation.

EXAMPLE 2

Micronised salmeterol xinafoate (9.57 mg) was weighed directly into an open aluminium can. 1,1,1,2-

Tetrafluoroethane (18.2 g) was added from a vacuum flask together with ethanol (0.455 g) and a metering valve was crimped into place. The resulting inhalers contained 9.57 mg salmeterol xinafoate (2.5% w/w ethanol) and delivered 50 microgram salmeterol per actuation.

EXAMPLE 4

Micronised fluticasone propionate (66 mg or 6.6 mg) is weighed directly into each of 100 open aluminium cans and a metering valve is then crimped into place on each can. Ethanol (0.182 g) and 1,1,1,2-tetrafluoroethane (18.2 g) is then added to each canister under pressure, through the valve, and each filled canister shaken to disperse the drug. The resulting inhalers contain 66 or 6.6 mg fluticasone propionate (1%.w/w ethanol) and deliver 250 or 25 microgram fluticasone propionate per actuation (Examples 3 and 4 respectively).

EXAMPLES 5 AND 6

Micronised salbutamol (24 mg or 48 mg) is weighed directly into each of 3 open aluminium cans. 1,1,1,2-Tetrafluoroethane (18.2 g) is added to each can from a vacuum flask together with ethanol (0.364 g), and a metering valve is then crimped into place. Each filled canister is then shaken in an ultrasonic bath for 8 minutes. The resulting inhalers contain 24 mg or 48 mg salbutamol (2% w/w ethanol) and deliver 100 or 200 microgram salbutamol per actuation (Examples 5 and 6 respectively).

EXAMPLE 7

Micronised salbutamol sulphate (15 mg) was weighed directly into an open aluminium can. 1,1,1,2-Tetrafluoroethane (18.2 g) was added from a vacuum flask together with ethanol (0.182 g) and a metering valve was then crimped into place. The filled canister was then shaken in an ultrasonic bath for 5 minutes. The resulting inhaler contained 15 mg salbutamol sulphate (1% w/w ethanol).

EXAMPLE 8

Isopentane (20 ml) was added to micronised salmeterol xinafoate (0.5 g) to form a slurry, which was sonicated for 3 minutes. The resulting suspension was dried by evaporating the isopentane at ambient temperature to yield surface-modified salmeterol xinafoate. Samples of this product (9.57 mg) are weighed into aluminium aerosol cans, ethanol (91 mg) and 1,1,1,2-tetrafluoroethane (18.2 g–99.95% w/w of total fill weight) is added and suitable metering valves are crimped onto the cans. The filled canisters are then each sonicated for 5 minutes. The resulting aerosols contained salmeterol in an amount equivalent to 240 actuations at 25 microgram per actuation (0.5% w/w ethanol).

EXAMPLE 9

Micronised beclomethasone dipropionate monohydrate (68 mg) is weighed into a clean, dry, plastic-coated glass bottle, 1,1,1,2-tetrafluoroethane (to 18.2 g) is added from a vacuum flask together with ethanol (0.182 g) and the bottle is quickly sealed with a metering valve. The resulting aerosol dispensed 250 microgram beclomethasone dipropionate (as the monohydrate) per 75.8 mg actuation (1% w/w ethanol).

EXAMPLE 10

Micronised sodium cromoglycate (1.2 g) is weighed directly into an aluminium can, 1,1,1,2-tetrafluoroethane (to 18.2 g) added from a vacuum flask together with ethanol (455 mg). A metering valve is crimped into place and the filled canister sonicated for five minutes. The aerosol delivers 5 mg sodium cromoglycate per actuation (2.5% w/w ethanol).

EXAMPLE 11

Micronised terbutaline sulphate (6.0 mg) is weighed directly into an aluminium can, 1,1,1,2-tetrafluorethane (to 18.2 g) added from a vacuum flask together with ethanol (91 mg). A metering valve is crimped into place and the filled canister sonicated for five minutes. The aerosol delivers 250 microgram terbutaline sulphate per actuation (0.5% w/w ethanol).

EXAMPLE 12

Micronised reproterol hydrochloride (120 mg) is weighed directly into an aluminium can, 1,1,1,2-tetrafluorethane (to 18.2 g) added from a vacuum flask together with ethanol (364 mg). A metering valve is crimped into place and the filled canister sonicated for five minutes. The aerosol delivers 500 microgram reproterol hydrochloride per actuation (2% w/w ethanol).

EXAMPLE 13

Micronised terbutaline sulphate (60 mg) is weighed directly into an aluminium can, 1,1,1,2,3,3,3-heptafluoro-n-propane (to 21.4 g) added from a vacuum flask together with ethanol (214 mg). A metering valve is crimped into place and the filled canister sonicated for five minutes. The aerosol delivers 250 microgram terbutaline sulphate per actuation (1% w/w ethanol).

EXAMPLE 14

Micronised salmeterol xinafoate (9.57 mg) is weighed directly into an aluminium can and 1,1,1,2,3;3,3-heptafluoro-n-propane (to 21.4 g) added from a vacuum flask together with ethanol (428 mg). A metering valve is crimped into place and the filled canister sonicated for five minutes. The aerosol delivers 25 microgram salmeterol xinafoate per actuation (2% w/w ethanol).

EXAMPLE 15

Micronised fluticasone propionate (13.3 mg) is weighed directly into an aluminium can, 1,1,1,2,3,3,3-heptafluoro-n-propane (to 21.4 g) added from a vacuum flask together with ethanol (107 mg). A metering valve is crimped into place and the filled canister sonicated for five minutes. The aerosol delivers 50 microgram fluticasone propionate per actuation (0.5% w/w ethanol).

EXAMPLE 16

Micronised salbutamol sulphate (31.7 mg) is weighed directly into an aluminium can, 1,1,1,2,3,3,3-heptafluoro-n-propane (to 21.4 g) added from a vacuum flask together with ethanol (535 mg). A metering valve is crimped into place and the filled canister sonicated for five minutes. The aerosol delivers 100 microgram salbutamol sulphate per actuation (2.5% w/w ethanol).

EXAMPLE 17

Micronised beclomethasone diproprionate (13.6 mg) is weighed directly into an aluminium can, 1,1,1,2,3,3,3-heptafluoro-n-propane (to 21.4 g) added from a vacuum flask together with ethanol (107 mg). A metering valve is crimped into place and the filled canister sonicated for five minutes. The aerosol delivers 50 microgram beclomethasone diproprionate per actuation (0.5% w/w ethanol).

EXAMPLE 18

|  | Per Inhaler % w/w | Per Actuation |
| --- | --- | --- |
| Salmeterol xinafoate | 0.048 | 36.25 microgram |
| Fluticasone propionate | 0.132 | 100 microgram |
| Ethanol | 1.0 | 0.76 mg |
| 1,1,1,2-Tetrafluoroethane | to 100 | to 75.8 mg |

EXAMPLE 19

|  | Per Inhaler % w/w | Per Actuation |
| --- | --- | --- |
| Salmeterol xinafoate | 0.048 | 36.25 microgram |
| Fluticasone propionate | 0.330 | 250 microgram |
| Ethanol | 2.5 | 1.9 mg |
| 1,1,1,2-Tetrafluoroethane | to 100 | to 75.8 mg |

EXAMPLE 20

|  | Per Inhaler % w/w | Per Actuation |
| --- | --- | --- |
| Salmeterol xinafoate | 0.048 | 36.25 microgram |
| Fluticasone propionate | 0.066 | 50 microgram |
| Ethanol | 0.5 | 0.38 mg |
| 1,1,1,2-Tetrafluoroethane | to 100 | to 75.8 mg |

EXAMPLE 21

|  | Per Inhaler % w/w | Per Actuation |
| --- | --- | --- |
| Salmeterol xinafoate | 0.048 | 36.25 microgram |
| Fluticasone propionate | 0.165 | 125 microgram |
| Ethanol | 1.0 | 0.76 mg |
| 1,1,1,2-Tetrafluoroethane | to 100 | to 75.8 mg |

EXAMPLE 22

|  | Per Inhaler % w/w | Per Actuation |
| --- | --- | --- |
| Salbutamol * | 0.132 | 100 microgram |
| Fluticasone propionate | 0.132 | 100 microgram |
| Ethanol | 1.0 | 0.76 mg |
| 1,1,1,2-Tetrafluoroethane | to 100 | to 75.8 mg |

* as free base or an equivalent weight of salt e.g. sulphate

EXAMPLE 23

|  | Per Inhaler % w/w | Per Actuation |
| --- | --- | --- |
| Salbutamol * | 0.264 | 200 microgram |
| Fluticasone propionate | 0.330 | 250 microgram |
| Ethanol | 2.0 | 1.52 mg |
| 1,1,1,2-Tetrafluoroethane | to 100 | to 75.8 mg |

* as free base or an equivalent weight of salt e.g. sulphate

EXAMPLE 24

|  | Per Inhaler % w/w | Per Actuation |
| --- | --- | --- |
| Salmeterol xinafoate | 0.048 | 36.25 microgram |
| Beclomethasone dipropionate | 0.066 | 50 microgram |
| Ethanol | 0.5 | 0.38 mg |
| 1,1,1,2-Tetrafluoroethane | to 100 | to 75.8 mg |

EXAMPLE 25

|  | Per Inhaler % w/w | Per Actuation |
| --- | --- | --- |
| Salmeterol xinafoate | 0.048 | 36.25 microgram |
| Fluticasone propionate | 0.264 | 200 microgram |
| Ethanol | 0.5 | 0.38 mg |
| 1,1,1,2-Tetrafluoroethane | to 100 | to 75.8 mg |

EXAMPLE 26

|  | Per Inhaler % w/w | Per Actuation |
| --- | --- | --- |
| Salbutamol * | 0.132 | 100 microgram |
| Beclomethasone dipropionate | 0.066 | 50 microgram |
| Ethanol | 2.0 | 1.52 mg |
| 1,1,1,2-Tetrafluoroethane | to 100 | to 75.8 mg |

* as free base or an equivalent weight of salt e.g. sulphate

EXAMPLE 27

|  | Per Inhaler % w/w | Per Actuation |
| --- | --- | --- |
| Salbutamol * | 0.264 | 200 microgram |
| Beclomethasone dipropionate | 0.264 | 200 microgram |
| Ethanol | 2.5 | 1.9 mg |
| 1,1,1,2-Tetrafluoroethane | to 100 | to 75.8 mg |

* as free base or an equivalent weight of salt e.g. sulphate

In Examples 18 to 27 micronised medicaments are weighed into aluminium cans, 1,1,1,2-tetrafluoroethane (18.2 g) is added from a vacuum flask, together with the ethanol, and metering valves are crimped into place.

We claim:

1. A pharmaceutical aerosol formulation consisting essentially of (i) particulate medicament, (ii) 1,1,1,2-tetrafluoroethane as propellant, and (iii) 0.01 to 5% w/w based upon the propellent of a polar cosolvent which is a $C_{2-5}$ aliphatic alcohol or polyol or a mixture thereof, the particulate medicament being present in an amount from 0.005% to 5% w/w relative to the total weight of the formulation and having a particle size of less than 100 microns, and which formulation contains less than 0.0001% w/w surfactant based upon the weight of medicament.

2. A formulation as claimed in claim 1, wherein the polar cosolvent is present in an amount from 0.05 to 3% w/w based upon the propellant.

3. A formulation as claimed in claim 2, wherein said medicament is an anti-allergic, a bronchodilator or an anti-inflammatory steroid.

4. A formulation as claimed in claim 2 wherein said medicament is selected from the group consisting of salmeterol, salbutamol, fluticasone propionate, beclomethasone dipropionate and physiologically acceptable salts and solvates thereof.

5. A formulation as claimed in claim 2 wherein said medicament is beclomethasone dipropionate or a physiologically acceptable solvate thereof.

6. A formulation as claimed in claim 2 wherein said medicament is selected from the group consisting of ephedrine, adrenaline, fenoterol, formoterol, isoprenaline, metaproterenol, phenylephrine, phenylpropanolamine, pirbuterol, reproterol rimiterol, terbutaline, isoetharine, tolubuterol, orciprenaline, (−)-4-amino-3,5-dichloro-α-[[[6-[2-(2-pyridinyl)ethoxy]hexyl]-amino]methyl]benzenemethanol and physiologically acceptable salts thereof.

7. A formulation as claimed in claim 2 which contains two or more particulate medicaments.

8. A formulation as claimed in claim 2 which contains a particulate bronchodilatory medicament and a particulate anti-inflammatory medicament.

9. A formulation as claimed in claim 2 which contains salmeterol xinafoate in combination with fluticasone propionate.

10. A formulation as claimed in claim 2 which is free of surfactant.

11. A formulation as claimed in claim 2 wherein the polar cosolvent is ethanol.

12. A formulation as claimed in claim 2 wherein the medicament is present in an amount from 0.01 to 1% w/w relative to the total weight of the formulation.

13. A formulation as claimed in claim 2 which has a respirable fraction of 20% or more by weight of the medicament.

14. A pharmaceutical aerosol formulation consisting of (i) particulate medicament, (ii) 1,1,1,2-tetrafluoroethane as propellant, and (iii) 0.01 to 5% w/w based upon the propellant of a polar cosolvent which is $C_{2-5}$ aliphatic alcohol or polyol or a mixture thereof, the particulate medicament being present in an amount from 0.005% to 5% w/w relative to the total weight of the formulation and having a particle size of less than 100 microns.

15. A formulation as claimed in claim 14 wherein the polar cosolvent is present in an amount from 0.05 to 3% w/w based upon the propellant.

16. A formulation as claimed in claim 15 wherein said medicament is selected from the group consisting of salmeterol, salbutamol, fluticasone propionate, beclomethasone dipropionate and physiologically acceptable salts and solvates thereof.

17. A formulation as claimed in claim 15 wherein said medicament is beclomethasone dipropionate or a physiologically acceptable solvate thereof.

18. A formulation as claimed in claim 15 wherein said medicament is selected from the group consisting of ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, (−)-4-amino-3,5-dichloro-α-[[[6-[2-2(pyridinyl)ethoxy]hexyl]-amino]methyl]benzenemethanol and physiologically acceptable salts thereof.

19. A formulation as claimed in claim 15 which contains two or more particulate medicaments.

20. A formulation as claimed in claim 15 which contains a particulate bronchodilatory medicament and a particulate anti-inflammatory medicament.

21. A formulation as claimed in claim 15 which contains salmeterol xinafoate in combination with fluticasone propionate.

22. A formulation as claimed in claim 15 wherein said medicament is an anti-allergic, a bronchodilator or an anti-inflammatory steroid.

23. A formulation as claimed in claim 15 wherein the polar cosolvent is ethanol.

24. A formulation as claimed in claim 15 wherein the medicament is present in an amount from 0.01 to 1% w/w relative to the total weight of the formulation.

25. A formulation as claimed in claim 15 which has a respirable fraction of 20% or more by weight of the medicament.

26. A formulation as claimed in claim 2 wherein the polar cosolvent is ethanol.

27. A formulation as claimed in claim 22 wherein the polar cosolvent is ethanol.

28. A pharmaceutical aerosol formulation consisting essentially of (i) particulate medicament, (ii) 1,1,1,2-tetrafluoroethane as propellant and (iii) 0.05 to 5% w/w based upon the propellant of a polar cosolvent being ethanol, isopropanol, propylene glycol or a mixture thereof, the particulate medicament being present in an amount from 0.01 to 1% w/w relative to the total weight of the formulation and having a particle size of less than 100 microns and which formulation contains less than 0.0001% w/w surfactant based upon the weight of medicament.

29. A formulation as claimed in claim 28 which is free of surfactant.

30. A formulation as claimed in claim 28 which contains 0.05 to 3% w/w based upon the propellant of a polar cosolvent.

31. A formulation as claimed in claim 29 which contains 0.05 to 3% w/w based upon the propellant of a polar cosolvent.

32. A formulation as claimed in claim 28 wherein the polar cosolvent is ethanol.

33. A formulation as claimed in claim 29 wherein the polar cosolvent is ethanol.

34. A formulation as claimed in claim 28 wherein said medicament is formoterol.

35. A formulation as claimed in claim 29 wherein said medicament is formoterol.

36. A pharmaceutical aerosol formulation consisting of (i) particulate medicament, (ii) 1,1,1,2-tetrafluoroethane as propellant and (iii) 0.05 to 5% w/w based upon the propellant of a polar cosolvent being ethanol, isopropanol, propylene glycol or a mixture thereof, the particulate medicament being present in an amount from 0.01 to 1% w/w relative to the total weight of the formulation and having a particle size of less than 100 microns.

37. A formulation as claimed in claim 36 which contains 0.05 to 3% w/w based upon the propellant of a polar cosolvent.

38. A formulation as claimed in claim 36 wherein the polar cosolvent is ethanol.

39. A formulation as claimed in claim 1 wherein the polar cosolvent is present in an amount of 0.05 to 5% w/w based upon the propellant.

40. A pharmaceutical aerosol formulation consisting of (i) a particulate medicament which is salmeterol or physiologically acceptable salts thereof, (ii) 1,1,1,2-tetrafluoroethane as propellant and (iii) 0.05 to 5% w/w based upon the propellant of a polar cosolvent being ethanol, isopropanol, propylene glycol or a mixture thereof, the particulate medicament being present in an amount from 0.01 to 1% w/w relative to the total weight of the formulation and having a particle size of less than 100 microns.

41. A formulation as claimed in claim 40 wherein the polar cosolvent is ethanol.

42. A formulation as claimed in claim 40 wherein the salmeterol is in the form of salmeterol xinafoate.

43. A formulation as claimed in claim 42 wherein the polar cosolvent is ethanol.

* * * * *

UNITED STATES PATENT AND TRADEMARK OFFICE
CERTIFICATE OF CORRECTION

PATENT NO. : 5,736,124
DATED : April 7, 1998
INVENTOR(S) : Akehurst et al.

It is certified that error appears in the above-identified patent and that said Letters Patent is hereby corrected as shown below:

Column 3,
Line 2, "beciomethasone" should be -- beclomethasone --;
Line 7, "solyates" should be -- solvates --;
Line 28, "propellanr" should be -- propellant --;
Line 38, "cromoglyeate" should be -- cromoglycate --.

Column 4,
Line 8, "pentone" should be -- pentane --.

Column 5,
Line 59, "$DF_{30}$" should be -- DF30 --.

Column 7,
Line 6, "EXAMPLE 4" should be -- Examples 3 and 4 --.

Column 8,
Line 7, "6.0" should be -- 60 --.

Column 11,
Line 8, there should be a comma after "reproterol";
Line 43, "solyates" should be -- solvates --.

Signed and Sealed this

Eighth Day of February, 2005

JON W. DUDAS
*Director of the United States Patent and Trademark Office*